United States Patent
Takahashi

(10) Patent No.: US 7,367,809 B2
(45) Date of Patent: May 6, 2008

(54) THREE-DIMENSIONAL DIGITAL ENTITY MESOSCOPE SYSTEM EQUIPPED WITH THREE-DIMENSIONAL VISUAL INSTRUCTION FUNCTIONS

(76) Inventor: Atsushi Takahashi, 20-15-1, Kizaki, Tsuruga-Shi, Fukui 914-0814 (JP)

( * ) Notice: Subject to any disclaimer, the term of this patent is extended or adjusted under 35 U.S.C. 154(b) by 0 days.

(21) Appl. No.: 10/594,193

(22) PCT Filed: Mar. 17, 2005

(86) PCT No.: PCT/JP2005/004758

§ 371 (c)(1),
(2), (4) Date: Dec. 7, 2006

(87) PCT Pub. No.: WO2005/093687

PCT Pub. Date: Oct. 6, 2005

(65) Prior Publication Data

US 2007/0184422 A1    Aug. 9, 2007

(30) Foreign Application Priority Data

Mar. 26, 2004    (JP) ............................. 2004-091349

(51) Int. Cl.
G09B 23/28 (2006.01)
(52) U.S. Cl. .................................................. 434/262
(58) Field of Classification Search ................ 434/262, 434/267, 268, 269, 270, 271, 272, 274, 275
See application file for complete search history.

(56) References Cited

U.S. PATENT DOCUMENTS

| | | | |
|---|---|---|---|
| 5,391,081 A * | 2/1995 | Lampotang et al. ........ 434/262 |
| 5,546,943 A * | 8/1996 | Gould ......................... 600/425 |
| 5,769,640 A * | 6/1998 | Jacobus et al. .............. 434/262 |
| 6,074,213 A * | 6/2000 | Hon ............................ 434/262 |
| 6,113,395 A * | 9/2000 | Hon ............................ 434/262 |
| 6,659,776 B1 * | 12/2003 | Aumann et al. ............. 434/262 |
| 6,739,877 B2 * | 5/2004 | Bailey et al. ................ 434/262 |
| 7,056,123 B2 * | 6/2006 | Gregorio et al. ............. 434/272 |
| 7,095,388 B2 * | 8/2006 | Truxa et al. .................... 345/7 |
| 7,249,951 B2 * | 7/2007 | Bevirt et al. ................. 434/262 |
| 2004/0064298 A1 * | 4/2004 | Levine ......................... 703/11 |
| 2005/0064378 A1 * | 3/2005 | Toly ............................ 434/262 |

* cited by examiner

Primary Examiner—Kurt Fernstrom
(74) Attorney, Agent, or Firm—Quintero Law Office

(57) ABSTRACT

The present invention provides a three-dimensional digital entity magnifying glass technique-assisting and training/educational distribution system incorporating three-dimensional visual training functions by means of image composition that enables a three-dimensional visual instruction containing a depth when giving visual instructions to an HMD worn by a medical practitioner to thereby display only images of a pointing device or various kinds of instruments among image information of the instructor's CCD camera and synchronously and compositely displaying a three-dimensional visual training image output from an image-processing apparatus that can display an after-image of the image for an arbitrary time setting into image information of the CCD camera, thereby providing equal-scaling display of image information to which an instruction and a comment by use of a visual display/instruction image are added three-dimensionally as well as an instrument actually used by the instructors (groups of lecturers) on the three-dimensional HMD of the medical practitioner.

16 Claims, 7 Drawing Sheets

THREE-DIMENSIONAL DIGITAL ENTITY MESOSCOPE SYSTEM EQUIPPED WITH THREE-DIMENSIONAL VISUAL INSTRUCTION FUNCTIONS

BACKGROUND OF THE INVENTION

1. Field of the Invention

The present invention relates to a system for performing technical training by utilizing a communication network such as the internet. More specifically, the invention relates to a system for distributing a highly precision oriented special technical educational program according to which a surgical operation or any other manual operation is performed under direct observation, performing educational training of highly precision oriented techniques by which a surgical operation or any other operation is performed by a specific customer (that is, such a surgical operation or other operations is controlled through visual instructions or oral instructions by use of three-dimensional image composition based on information obtained while a visual field of a person with no technical knowledge assumed to be a robot from a remote location), or providing image information of an invisible region together with a direct surgical field image to a visual perception visual field of a surgical operation without a need for the medical practitioner to take his eyes off the surgical field.

2. Description of the Related Art

Generally, in the case of providing training regarding a surgical operation or any other special manual technique in the clinical field, a medical practitioner and an instructor face different visual field directions and adopt different postures, and it is thus difficult to provide training regarding manual technique such as accurate instrumentation, which not only increases operation time but also causes the instructor to block the medical practitioner's view so that the operation may have to be interrupted temporarily; further, it may also cause a patient to feel uneasy in a conscious operating environment and suffer from a psychogenic shock.

Conversely, in the case of instructing a student to perform a highly precision oriented technique such as a surgical operation by an instructor, if the technique and the surgical operation on a closed site are to be observed from identical ideal visual field as the instructing medical practitioner (lecturer), in order to permit a plurality of students (customers) to sequentially observe an operating situation at each step of the surgical operation, not only extremely much of time is required but also the number of persons who can observe the operation simultaneously is limited by the physical constraints of the facilities used for the operation, and such lectures have been observed by very few people. In addition, if the instructing medical practitioner (lecturer) and the student (customer) speak different languages, an interpreter needs to be present during the surgical procedure, so that a fee per student (customer) for participating in such an educational program has been expensive.

Moreover, both in the case of instructing a medical practitioner and the case of an instructor instructing a student, an operator needs to once take his eyes off a surgical field and closely watch and confirm information such as an X-ray picture, a CT picture, an MRI picture, or an electrocardiogram, so that it has been difficult to share the information with others especially at a remote location in real time.

Further, in the case of a surgical operation, it is difficult to transport a patient himself to a remote location for an educational program; also, in the case of other special techniques performed by hand which require large facilities or unmovable instruments, a visiting student used to arrange his schedule so as to fit in with the operating date and spend much transportation costs and time required by transportation. Also, in the case of distributing an educational program to a remote location by using various types of communication means, if a surgical operation on an individual is to be disclosed to a third party fundamentally, to obtain consent of a patient himself for responsibility of privacy protection, of course, the much the same responsibility is imposed on information so prevent it from being leaked along a communication path. Conversely, in the case of training on a surgical operation or a practical training of highly precision oriented operation which is performed at a remote location, instructors (groups of lecturers) must go to a spot that requires a lot of costs, so that various costs (transportation costs and time required by transportation) related to the training and, moreover, the remote area requiring much time to go there could not easily accommodate performing of an emergency surgical operation; especially in the case of training by a plurality of instructors (groups of lecturers), the costs involved have swollen even further and an emergency surgical operation has proved even more difficult to conduct.

Furthermore, it is prohibited by medical licensing legal regulations to conduct medical operation abroad, so that it is basically impossible to conduct a lecture of a live operation visiting educational program and practical training of a surgical operation by which the instructors (groups of lecturers) themselves perform the surgical operation abroad.

Further, if a medical practitioner (customer) actually wishes to be trained in a surgical operation or any other highly precision oriented techniques conducted manually, it is essentially impossible to gather instructors (groups of lecturers) and persons with excellent skills and knowledge who are scattered around to one place at the same date and time so that a surgical operation may be edited or managed. Furthermore, there has been no system for discussing a shared three-dimensional image while displaying a three-dimensional instruction image.

Patent Document 1 Japanese Patent Application No. 2556829.

BRIEF SUMMARY OF THE INVENTION

However, as described above, in the case of instructing a surgical operation or any other specialized manual techniques at a clinical field, generally an instructor would share identical visual field as a medical practitioner to conduct accurate training, thereby preventing required surgery time from increasing. Furthermore, even in the case of conscious operating environments, what should be kept in mind is to avoid a patient from being worried about the existence of the instructor so that he may not feel uneasy unnecessarily.

In contrast, in the case of training students on highly precision oriented techniques such as a surgical operation which is conducted by an instructor, if the students are permitted to watch the techniques and the surgical operation conducted on a closed site of the body from identical ideal visual field as the instructing medical practitioners (lecturers), many people are enabled to view the field. In addition, if the instructing medical practitioner (lecturer) and the student (customer) speak different languages, a need is eliminated for causing an interpreter to be present during the surgical procedure all the way, thereby avoiding an increase in a fee per student (customer) for participating in such an educational program.

Moreover, also in the case of training a medical practitioner and the case of an instructor training a student, an operator is enabled to view and confirm the information such as an X-ray picture, a CT picture, an MRI picture, and an electrocardiogram without taking his eyes off the surgical field and also share the information even at a remote location in real time.

Further, in the case of a surgical operation, a patient need not go to a remote location to participate in an educational program, to instead reduce transportation fees of a visiting student (customer) and time required by the transportation. Also in the case of distributing the program to a remote location by using the various types of communication means, information about individuals are prevented from being leaked. Conversely, in the case of conducting practical training on highly precision oriented operation or training on a surgical operation at a remote location, it is made possible to reduce various costs (transportation costs and time required by the transportation) of the instructors (group of lecturers) and accommodate performing of an emergency surgical operation at a remote location which requires much of time to go there and, additionally, conduct training by a plurality of instructors (groups of lecturers). Besides, it is made possible to avoid medical licensing legal regulations and conduct a lecture of a live operation visiting educational program and practical training of a surgical operation by which the instructors (groups of lecturers) themselves perform the surgical operation abroad.

Further, if a medical practitioner (customer) actually wishes to be trained in a surgical operation or any other highly precision oriented techniques conducted manually, it is made possible to gather instructors (groups of lecturers) and persons with excellent skills and knowledge who are scattered around to one place at the same date and time so that a surgical operation may be edited or managed and, furthermore, discuss their shared three-dimensional images in real time.

The present invention provides a system that provides a three-dimensional digital entity magnifying glass with a variety of functions, for performing an assistance and training/educational program for surgical operations and other highly precision oriented techniques which are performed under direct observation of a human being, by using the internet or an intranet as communication means, the system incorporating a three-dimensional visual training function for using an apparatus comprised of three-dimensional telescopic digital magnifying glass which are constituted of a pair of LCDs which are set in front of the two eyes and have identical synchronized standards, as a minimum configuration, so as to be worn by a medical practitioner and a instructor when performing the assistance and training/educational program for surgical operations and other highly precision oriented techniques and three-dimensional telescopic digital magnifying glass constituted of an automatic focusing CCD camera equipped with a pair of zoom lenses which are set from a position that corresponds to a center between the right and left pupils of workers wearing the three-dimensional digital entity magnifying glass constituted of the LCDs in front thereof in a direction toward a visual field of the naked eye, to extract only a three-dimensional image of a three-dimensional pointing device or various types of instruments (dummies) identical to instruments used by the medical practitioner that can be held and freely moved within the visual field of the instructor and is operated by the instructor for giving visual instructions as recognizing on an LCD monitor of a three-dimensional digital entity magnifying glass apparatus in front of a background having a single color of red, green, and blue (red is preferable in the mouse cavity because it is complementary to a color of the blood vessel and the fresh) in consideration of a complementary color relationship corresponding to a background color of a visual field image among the R, G, and B colors which are set so as to cover an entire visual field in front of the CCD camera of the three-dimensional digital entity magnifying glass apparatus worn by the instructor captured by the CCD camera of the three-dimensional digital entity magnifying glass apparatus worn by the instructor with a floater-image-processing apparatus on a three-dimensional image of the visual field of the medical practitioner captured by the CCD camera of the three-dimensional digital entity magnifying glass apparatus worn by the medical practitioner shared in display by the three-dimensional digital entity magnifying glasses of both the medical practitioner and the instructor and, further, change a degree of transparency, between 0% and 100%, of three-dimensional visual instruction floater images due to an image chroma-key composite image-processing apparatus or convert them so that their tint may be judged and display a resultant composite image on the LCDs of both the medical practitioner and the instructor. By this three-dimensional digital entity magnifying glass system, the medical practitioner or the instructing medical practitioner can obtain an ideal camera angle when imaging and observing a surgical field without taking his eyes off the surgical field and without the head of the medical practitioner blocking his view and, therefore, can concentrate on a surgical operation without being worried about a camera position.

Of course, this action of instruction can be instructed by the instructor at a location away from an operating environment and so is performed without being perceived by a patient so that he may not be mentally influenced unnecessarily; moreover, the medical practitioner not only can be trained by the instructor through a simulation having a reality by expressing, in a working space over images of an entity (patient) on the LCD of the medical practitioner, also a three-dimensional depth of a three-dimensional image of the same instrument as that actually used by the medical practitioner operated by the instructor in a medical practitioner's visual field image virtual space of the instructor's three-dimensional digital entity magnifying glass for the entity before the eyes which is captured on the tree-dimensional digital entity magnifying glass visual field screen worn by the medical practitioner but also apparently can generate visually an operating situation in which he operates himself by using the same instrument, so that even poor verbal communication between the medical practitioner and the instructor can be sufficiently compensated for visually.

By conducting thus practical educational training services involving visual instructions, time-wise expenses involved in transportation of one a plurality of instructors (groups of lecturers) can be eliminated, thereby accommodating an emergency operation even at a remote location.

Further, in a surgical operation, a student (customer) can be trained across the border without transporting a patient from arbitrary operating facilities and without medical licensing regulations even if an instructing medical practitioner (lecturer) of an educational program and the student (customer). By further improving this three-dimensional digital entity magnifying glass apparatus to compositely display three-dimensional image information obtained through image processing/conversion by changing a three-dimensional anatomical image of the bone, the blood vessel, the nervous tissue, etc. created beforehand from information of a tomogram such as a CT picture or an MRI picture of a patient on whom an operation is to be performed or a surgical stent image into which the anatomical three-dimensional perspective image are three-dimensionally composed together with a dissection or bone cutting position similarly by a percentage of between 0% and 100%, especially, changing a degree of transparency or a color tone of a site or a tissue indicative of an anatomical landmark or giving a visual difference to the medical practitioner's three-dimensional digital entity magnifying glass CCD image information through wireframe display etc. so as to facilitate discrimination, the medical practitioner can visually watch shapes of the blood vessels and the bones as if by seeing through the skin or the soft tissues and further watch how the nerves run through the bones as if seeing through the bones and, therefore, can safely perform a surgical operation accurately. However, it may be possible that both a medical practitioner wearing an HMD and the subject of a surgical operation always change in three-dimensional position. To solve this problem, it is necessary to superimpose the three-dimensional anatomical image or surgical stent image accurately on an image of a surgical field displayed on the medical practitioner's HMD so that the three-dimensional anatomical image or surgical stent image may follow the image of the surgical field captured by the medical practitioner's CCD camera, based on a change in position of the head of the medical practitioner and a change in posture of the patient. To make such a configuration clinically applicable, still images are taken out from a medical practitioner's visual field image picked up by the two mutually synchronized right and left CCD cameras of the medical practitioner's three-dimensional digital entity magnifying glass and a reference point is set to three positions on an anatomically universal hard tissue such as a tooth or a bone on each of these images, position information of a total of six points, three points each, is recorded. By recording a three-dimensional positional relationship between a medical practitioner and a patient through three-point measurement by use of these two right and left CCD cameras and following positional movements of the three points that provide a reference in a medical practitioner's visual field image (moving image), it is possible to always grasp a three-dimensional positional change in the three-dimensional digital entity magnifying glass and a posture of the patient. At the same time, by accurately plotting the same three points as those that provide a reference over an anatomically universal hard tissue on a three-dimensional anatomical image or a surgical stent image on three points of the hard tissue of still images taken out from information from the two CCD cameras of the medical practitioner's three-dimensional digital entity magnifying glass and accurately superimposing the three-dimensional anatomical image or the surgical stent image in an image of a surgical field, a three-dimensional position, in a three-dimensional image of the surgical field, of the three-dimensional anatomical image or the surgical stent image is recorded in a space of a space of the surgical field captured by the medical practitioner's three-dimensional digital entity magnifying glass. It is thus possible to three-dimensionally follow the three-dimensional anatomical image or the surgical stent image as three-dimensional positions move of the patient and the medical practitioner's three-dimensional digital entity magnifying glass.

These three-dimensional anatomical image and surgical stent image can be managed and operated in a consolidated manner at a remote location. For example, in an emergency operation required in an area far away from a family doctor, a medical practitioner can transmit with various types of communication means information, of a patient just about to be operated, from the right and left CCD cameras captured through a three-dimensional digital entity magnifying glass, take out an arbitrary still image from the information received at a remote location (information from the right and left CCD cameras captured through the medical practitioner's three-dimensional digital entity magnifying glass), superimpose a three-dimensional anatomical image or a surgical stent image on this still image so as to perform positional correction, perform computer processing on a positional change in information of an image of a surgical field to follow, based on the three-dimensional movement, the three-dimensional anatomical image or surgical stent image, and then transmit a thus superimposed composite image and display it as a three-dimensional image on a three-dimensional digital entity magnifying glass LCD mounted on the medical practitioner.

Further, in the present system, not only a face-to-face combination of a medical practitioner and an instructor but also a plurality of instructors can simultaneously display a three-dimensional anatomical image or a surgical stent image or participate in three-dimensional visual training. In such a training situation, the medical practitioner as well as the plurality of instructors can assume an image of a medical practitioner's visual field as one table to thereby exchange comments about various specialized categories on this table, in which case real rights to manage the table can be operated in accordance with predetermined priority order to easily manage and operate the shared table (display screen) without confusion.

Similarly, by transmitting three-dimensional image information captured by CCD cameras of the three-dimensional digital entity magnifying glass CCD mounted on a medical practitioner through communication means such as the internet or an intranet and accumulating it in a server, a plurality of persons on which mutually synchronized three-dimensional digital magnifying glasses are mounted respectively can share that image information by using communication means such as the internet or the intranet. The relevant images, which have been accumulated moving images though, are of a visual field of a surgical field obtained when a medical practitioner actually performed a surgical operation and so can be such as to have an extremely high degree of reality with a feeling of sensation. Moreover, by permitting each of these multiple viewers to arbitrarily make switchover between a display mode and a non-display mode of images accumulated in the server together with surgical field image information shared by these viewers such as three-dimensional anatomical images of the arbitrary bones, blood vessels, and nervous tissues produced on the basis of tomographic information such as CT or MRI of a patient to be operated, the anatomical three-dimensional perspective images, and surgical stent images obtained by accurately composing three-dimensionally a position of dissection and bone cutting by using an image position-correction and follow-up apparatus, it is possible to demonstrate a surgical operation with more information. In addition, by removing with a floater-image-processing apparatus a background image from a viewer's visual field image obtained by utilizing the CCD cameras of the three-dimensional digital entity magnifying glass to extract an image of only a three-dimensional pointing device operated by the viewer or various types of instruments (dummies) identical to those used by the medical practitioner and change the degree of transparency by a percentage of between 0% and 100% to provide a floating image whose tint has been changed for each of the viewers and chroma-key composing it on an accumulated image in an image due to the three-dimensional digital entity magnifying glass mounted as viewing means for each of the viewers in condition where each of the viewers can switch between the display mode and the non-display mode arbitrarily, it is possible to carry out bidirectional discussion or operation simulation on a three-dimensional moving image or still image by utilizing a communication line such as the internet.

Further, in a case where a surgical operation is distributed and published to third parties at a remote location by using various types of communication means, as for a problem of privacy of a patient, his security can be realized by limiting access by using a password, performing different types of image scrambling (encryption) through two channels through which three-dimensional images are provided to subsequently performing software-wise decoding information in a personal computer used as this communication apparatus, mounting an integrated circuit having decoding functions in hardware of a three-dimensional digital entity magnifying glass, or identifying a code number assigned to the three-dimensional digital entity magnifying glass (terminal). Furthermore, through publication of such information in accordance with certain constraints, it is possible not only to contribute to developments of various technologies but also to find competent technicians (medical doctors) and instantaneously diffuse the latest excellent techniques worldwide.

Moreover, when an instructor or a assistant is selected by using extremely large amount of information and a three-dimensional digital entity magnifying glass capable of inspection, instruction, and recording and in virtual experiences of an operating situation of a medical practitioner, it is possible to provide a site of the network where information can be exchanged, without restrictions on an area and time. Besides, since skills can be assessed objectively, when a medical practitioner buys an assistance and training/educational program, it is possible to present highly authentic evaluation criteria by a third party institution as well as one-directional promos of the instructor (lecturer) or subjective evaluation by an acquaintance who participated in the program already; therefore, it is possible not only to easily give justification to evaluation and fees about technical training but also to, when selecting an instructor (assistant), present monetary rewards as well as conditions such as skills and experiences for each technical field or a language spoken in training, thereby easily selecting a well-qualified person most suitable for details of a surgical operation to be performed.

When a monetary contract is signed with such a registered medical doctor or technician on the network and if breach of contract occurred on the side of a medical practitioner or an instructor in training of a surgical operation or helping, such a system can be configured that resultant damages may be charged in accordance with contents of the contract already signed; accordingly, by this contract already established upon application, which has been signed by the medical practitioner and the instructor not acquainted with each other though, the well-qualified person (instructor) awaiting at a remote location or the medical practitioner can accept a temporary staff at ease and, moreover, a manager of the network who promotes a procedure for this application can cause beforehand the medical practitioner to select second-choice and third-choice persons of the instructor (assistant) so that essential damages on the side of the medical practitioner may be compensated for, thereby avoiding a trouble through discounting in accordance with skills of the instructor in some cases.

Further, if an unexpected situation such as an error in medical treatment occurred in an action of operating involving an instructor (assistant) using a three-dimensional digital entity magnifying glass system, it is of course possible to easily clarify an erroneous position based on a record of information by the three-dimensional digital entity magnifying glass and also to give variations in scope responsibility and guide fee to contents of the contract beforehand in accordance with a degree of difficulty of each of operations or a degree of involvement corresponding to each of technical fields of the instructor or the assistant and clarify the responsibility range corresponding to a training fee presented by the medical practitioner in accordance with the contents of the contract; it is thus possible not only to disperse risks of compensation for an error in medical treatment or a defect but also to add such factors as skills of the medical practitioner, which provide criteria for insurance fees of a typical term insurance and also a degree of difficulty of a case as well as skills of the instructor (assistant) and an establishment (number of persons) for each operation so that more essentially streamlined setting of insurance fees may be performed, which basis for calculation of the insurance fees can be improved in terms of accuracy by accumulating experiences and achievements (success rate or time-wise survival rate) through use of the present system by the medical practitioner and the instructor (assistant).

As described above, this three-dimensional digital entity magnifying glass enables virtually experiencing an operating situation of a medical practitioner; the three-dimensional digital entity magnifying glass system gives extremely large amount of information of skills of an instructor and so enables virtually observing an operating situation of the instructor in real time and also with an extremely high degree of authenticity due to a system that can be communicated only with three-dimensional digital entity magnifying glasses of identical standards and, further, can record the situation in a recording medium so that the skills may be evaluated objectively. Therefore, in the conventional case of auditing an action of medical treatment in a medical treatment field, conventional contents of auditing only matching between diagnosed contents and the action of treatment can be expanded further to objectively evaluate a surgical field (personal skills of medical doctor), thereby improving not only the skills of each of the medical doctors but also technical levels as a whole.

In a surgical operation actually performed by a medical practitioner, of course, a three-dimensional anatomical image composed and displayed in a medical practitioner's visual field image, a surgical stent image, or an instructor image of a plurality of instructors interferes with a visual field image commonly owned by the medical practitioner and the instructor, so that by enabling a display mode operation and a non-display mode operation with switching that will not block operations of using the hand or foot involved in an action of operating by the medical practitioner or the instructor through wishes of the medical practitioner or the instructor, it is possible to carry out a safe operation by utilizing features of the three-dimensional digital entity magnifying glass as a pure digital magnifying glass without blocking a view of the medical practitioner.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

An embodiment of the present invention will be described below together with illustrated examples.

Figure 1:
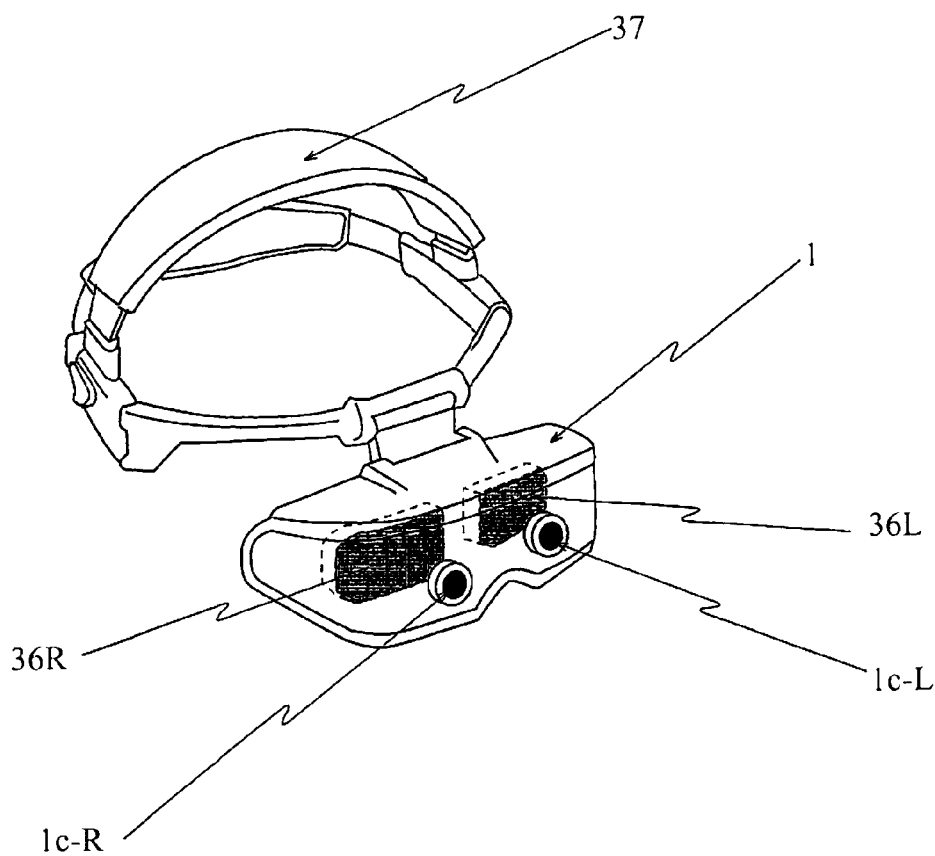
FIG. 1 is an illustration showing a configuration of a three-dimensional digital entity magnifying glass.

Throughout the drawings, the same symbols indicate the same components. FIG. 1 is an illustration showing a basic configuration of a three-dimensional digital entity magnifying glass 1. As shown in FIG. 1, a right-side LCD36R (monitor) and a left-side LCD36L installed in the three-dimensional digital entity magnifying glass 1 have a spread that contains the respective right and left eyes of a medical practitioner 3, which may be an instructor or a person to be instructed and mounted on the head (face) by using a headgear 37. A right-side CCD camera 1c-R and a left-side CCD camera 1c-L are provided integrally with the three-dimensional digital entity magnifying glass 1 to a position that nearly corresponds to a central section between the right and left pupils in condition where their three-dimensional digital entity magnifying glass 1 is mounted on the face. It should be noted that image information from each of these two CCD cameras 1c is used to give synchronized individual images on right and left CDs, thereby providing a three-dimensional image with little uncomfortable feeling in much the same manner as in condition where an optical magnifying glass is used.

Preferably the CCD camera 1c is an automatic focusing CCD camera equipped with a zoom lens. This type of camera is automatically adjusted to give appropriate focusing for an arbitrary magnification setting irrespective of a distance between the head of a worker and a work site, so that a medical practitioner can minimize muscle fatigue of his neck owing to fixation of the headgear-mounted head.

Figure 2:
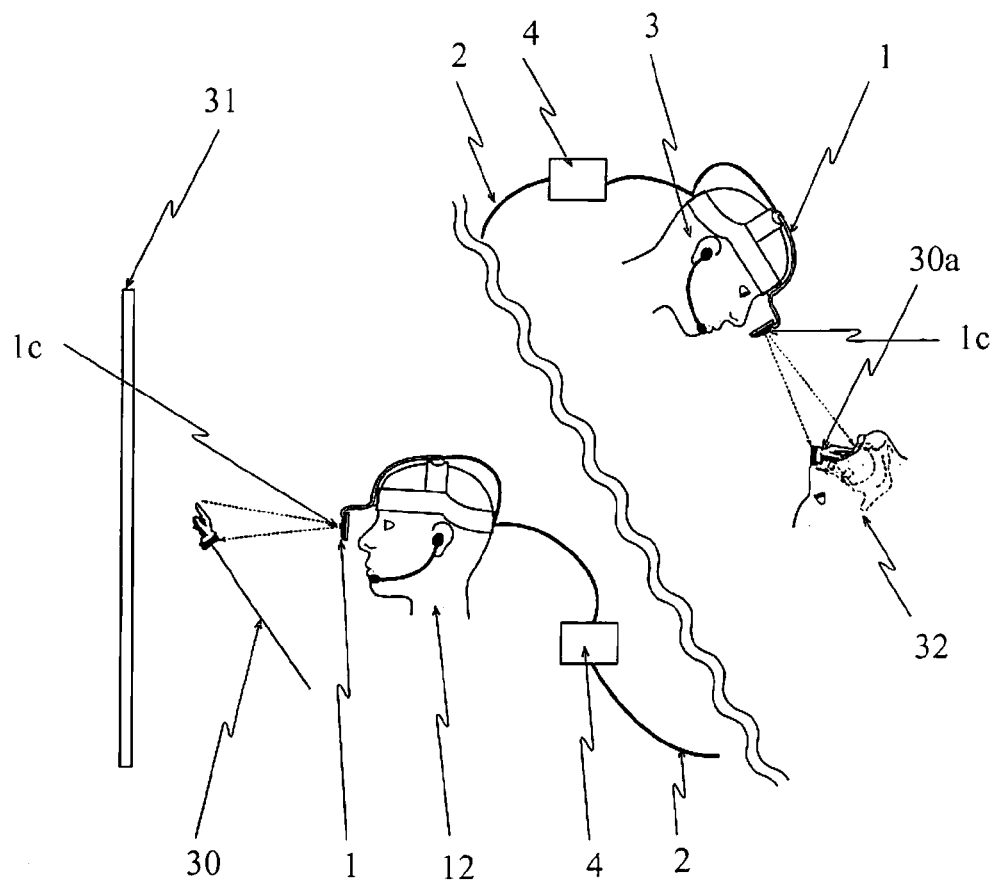
FIG. 2 is a conceptual illustration of performing of three-dimensional instruction by use of chroma-key composition of a floating image by utilizing three-dimensional digital entity magnifying glasses of identical standards.

In this configuration, as shown in FIG. 2, by utilizing a system of such a three-dimensional digital entity magnifying glass 1 to project images due to image information of each of the right and left two CCD cameras 1c on the medical practitioner 3 to the respective LCDs of the three-dimensional digital entity magnifying glasses having identical standards and mounted on the medical practitioner 3 and an instructor 12 so that they may share a three-dimensional visual field image (image of an inside of the mouth cavity of a patient 32). On this shared medical practitioner's visual field image, a virtual three-dimensional instruction mark (virtual image) 30a is chroma-key composed which is obtained by imaging a three-dimensional instruction mark 30 in front of a monochromatic background plate 31 by utilizing the right and left CCD cameras 1c of the three-dimensional digital entity magnifying glass 1 mounted on the instructor 12 and floating it. This three-dimensional instruction mark 30 can be displayed as a line drawing in a visual field image of the medical practitioner 3 by showing a trajectory for a constant lapse of time or displayed as a still image.

Accordingly, the present system, which is comparatively simple but uses the CCDLCD monitors of identical standards, permits the instructor 12 to accurately give a three-dimensional image instruction to the medical practitioner without performing complicated correction. That is, the medical practitioner 3 can provide training with an extremely natural posture almost identical to that in a case where he actually performs a surgical operation using his own hands, different from such movements as those for giving instructions on a computer monitor conventionally. Even in a case where this three-dimensional instruction mark 30 is replaced with an actual operating instrument, the instructor 12 can perform in a medical practitioner's visual field virtual space the same manipulations as those in the case of actually performing a surgical operation to a surgical field developed on an LCD screen of the three-dimensional digital entity magnifying glass 1 mounted on himself. Similarly, the medical practitioner 3 can experience manipulations of an instrument having a three-dimensional depth in such a situation as if he himself were performing a surgical operation. Furthermore, by changing a degree of transparency between 0% and 100% of three-dimensional visual instruction floating images of the instructor 12 which are composed and displayed in a visual field image of the medical practitioner 3 or, in addition to it, using a chroma-key composite image-processing apparatus capable of tint conversion, it is possible to easily distinguish between a real image and a virtual image, thereby avoiding a confusion on the monitor screen even in a case where the medical practitioner 3 and the instructor 12 use the same instruments.

Figure 4:
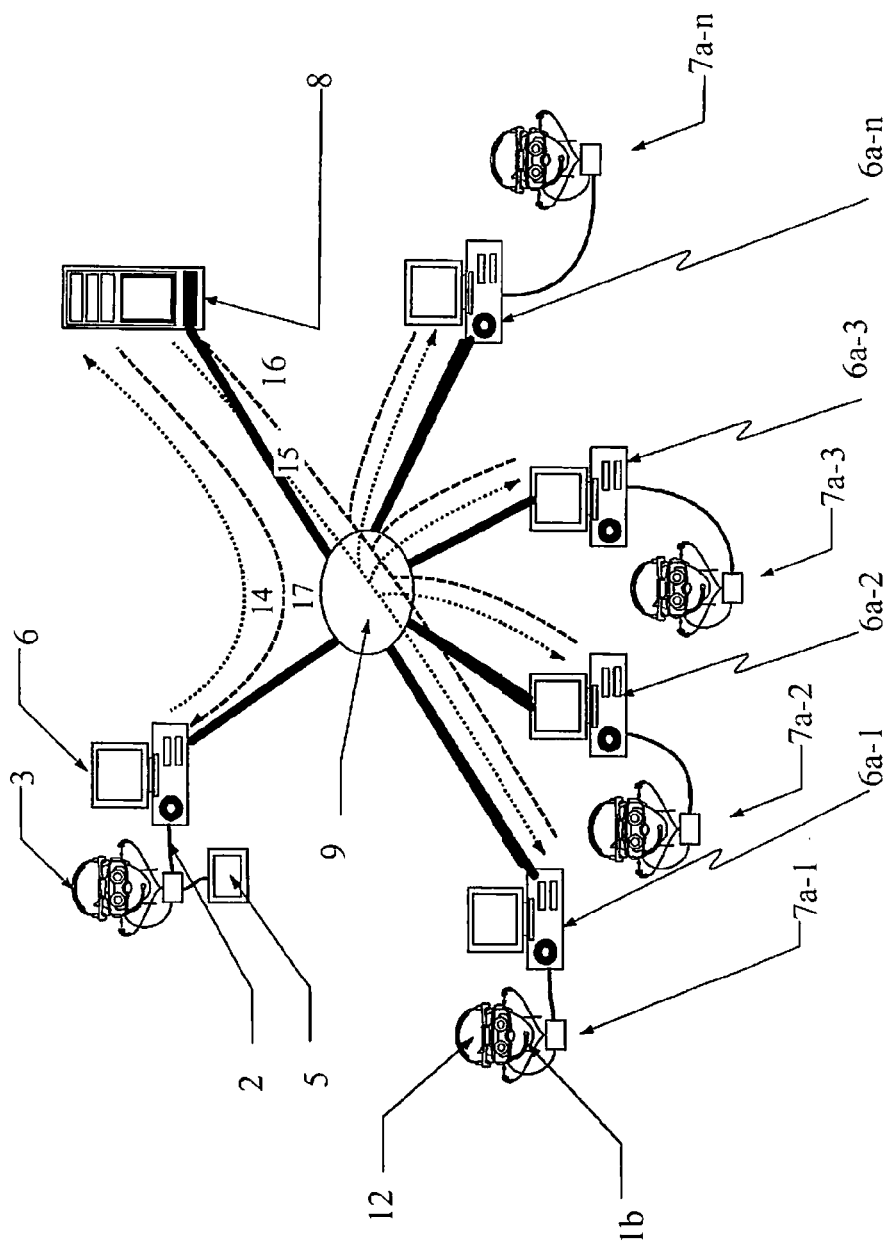
FIG. 4 is a conceptual illustration of a plurality of instructors carrying out a configuration of FIG. 3.
Figure 5:
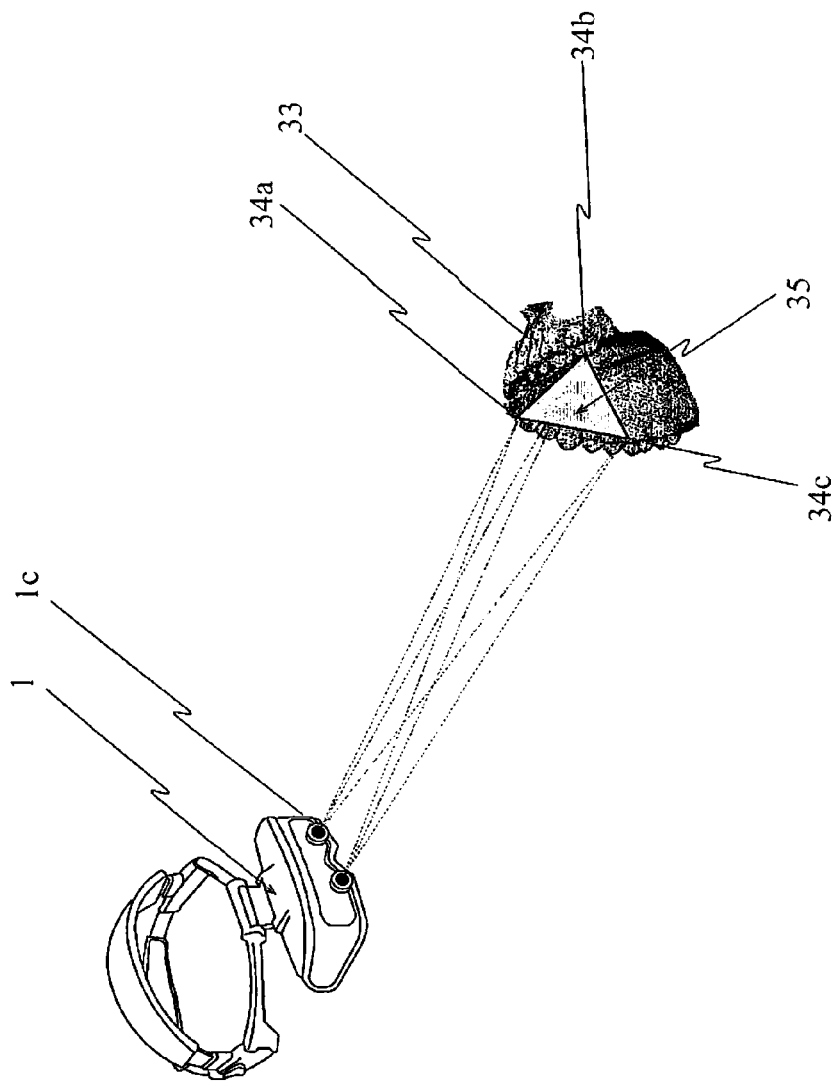
FIG. 5 is a conceptual illustration of three-dimensional positional measurement by use of a fixed base plane image.
Figure 6:
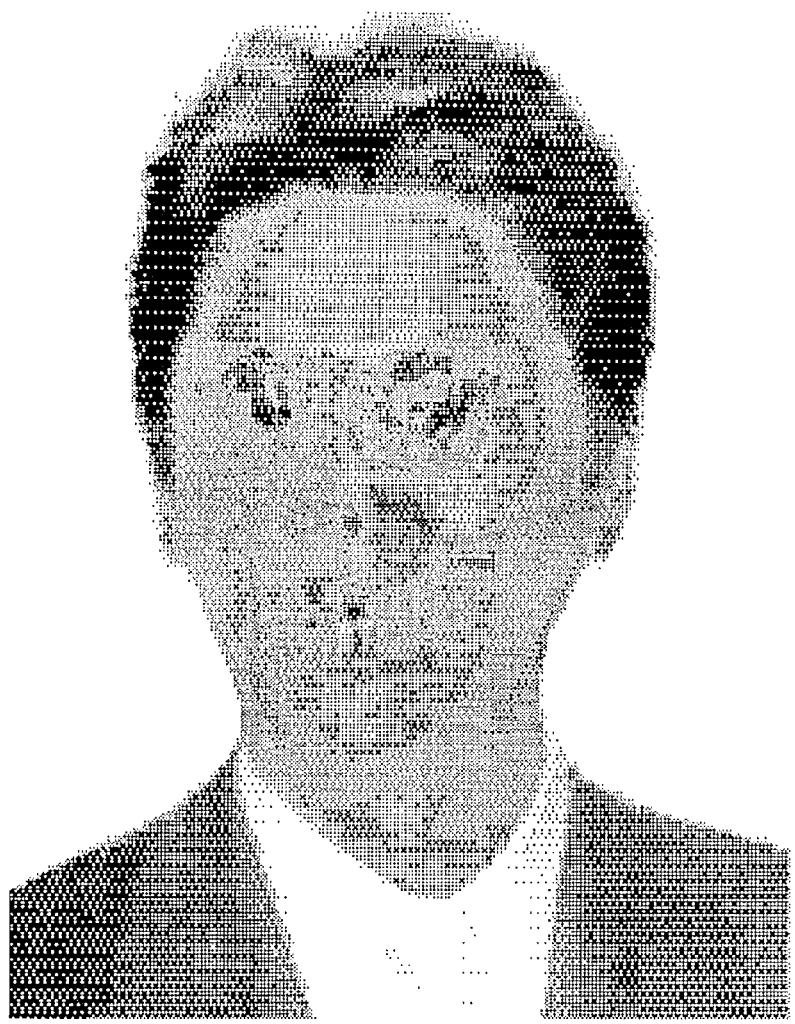
FIG. 6 shows how anatomical images can be composed and displayed.

Similar to this chroma-key composition of instruction images, three-dimensional anatomical images and surgical stent images saved in a personal computer 6 and personal computers 6a-1 through 6a-n or a server 8 shown in FIG. 4 can be chroma-key composed on a medical practitioner's visual field image and displayed. In this case, three-dimensional anatomical images and surgical stent images can also undergo image processing conversion by a percentage of between 0% and 100%, alteration of a degree of transparency or a color tone, or wireframe processing to easily apply visual differences to image information from the three-dimensional digital entity magnifying glass CCDs on the medical practitioner. Three hard tissue reference points 34a-34c on a tooth in a patent's tooth row 33 from a still image among image information from the medical practitioner's three-dimensional digital entity magnifying glass CCDs such as shown in FIG. 5 and the same hard tissue reference point on a tooth in a tooth row 7 on the patient's three-dimensional anatomical image or the three-dimensional surgical stent image are selected and plotted using the personal computers 6 or 6a-1 through 6a-n or the server 8, to accurately superimpose such three-dimensional anatomical images and surgical stent image layers into the visual field image of the medical practitioner 3 in such a manner as to be equally scaled down on the LCDs of the three-dimensional digital entity magnifying glasses 1 mounted on the medical practitioner 3 and the instructor 12 shown in FIG. 1 as a transparent image such as shown in FIG. 6 and, at the same time, perform three-dimensional position correction in them. In such scaling correction and position correction, in a case where it is difficult to directly obtain a hard tissue reference point depending on a site, a point marker such as lead is stuck to three different fixed points on the skin which are visible from the CCD cameras of the three-dimensional digital entity magnifying glass 1 at the time of performing a surgical operation during taking a CT or MRI picture and displayed on a three-dimensional surgical stent so that the corresponding on-the-skin different three-point markers on the respective still images from the right-side CCD camera 1c-R and the left-side CCD camera 1c-L for displaying a surgical field image of the three-dimensional digital entity magnifying glass 1 may agree with each other, thereby accurately performing position correction. In this case, although it is difficult to perform position correction and equal-scaling correction simultaneously on the right and left LCDs, in the three-dimensional digital entity magnifying glass 1 of the present invention, the right-side LCD monitor and the left-side and CCD camera are of identical standards, so that by performing equal-scaling work on either one of the right and left LCD screens and then conducting position correction (superimposition) on the one-side LCD monitor in different two directions, it is possible to easily record position information. Further, if a site to be operated is the head, especially, covers the upper and lower jaws, three different reference points are obtained for each of the sites and two different surgical stents are prepared, to automatically follow the respective floating surgical stent images.

A three-dimensional anatomical image layer or a three-dimensional surgical stent layer image, if it has undergone scaling correction and position correction once, is composed into a medical practitioner's visual field image and displayed by capturing a displacement of a three-dimensional positional measurement reference plane 35 made up of three hard tissue reference points 34a-34c on the tooth in the tooth row 33 as image information for the right and left two CCDs 1c of the three-dimensional digital entity magnifying glass 1 on the medical practitioner 3, performing three-dimensional positional measurement thereon by using the personal computers 6 and 6a-1 through 6a-n or the server 8, and following the point markers such as lead or the reference points on the image as the position of the medical practitioner's CCD camera and the posture of the patient change to automatically perform three-dimensional position correction thereon in real time. In this case, a change in posture of the patient may be captured by utilizing an image as described above or mounting a light emitter such as an LED to the three different points attached on the universal tissue of the head of the patient in order to more clearly display the reference points on the image. Alternatively, a gyro mechanism may be mounted to each of a fixed point such as the patient's hard tissue or the three-dimensional digital entity magnifying glass mounted on the medical practitioner to record a change in three-dimensional position of the patient and the medical practitioner's three-dimensional digital entity magnifying glass with respect to the fixed point (reference point) and accurately align it with the reference point on a still image due to information from the right and left CCD cameras obtained from the medical practitioner's three-dimensional digital entity magnifying glass so that an initially-corrected three-dimensional anatomical image or three-dimensional surgical stent image may be followed three-dimensionally as the patient's posture changes or the head of the medical practitioner moves.

By improving this system, it is possible to share medical practitioner's images among a plurality of instructors as shown in FIG. 4 so that medical specialists may give an appropriate advice. This advice is shared by the medical practitioner 3 and all of the instructors 12 by captioning a signal from a vital sign measuring instrument 5 at a peripheral of the LCD monitor of the three-dimensional digital entity magnifying glass 1 in such a manner as not to damage an image of a surgical field, so that it is possible for the instructors not only to provide an instruction as grasping a field situation more accurately but also for the medical practitioner 3 to concentrate on a surgical operation without taking his eyes off the surgical field to the monitor etc.

Further, in the case of transmitting through a communication network such as the internet image information obtained by providing identical image as that on the three-dimensional digital entity magnifying glass with advices and comments due to writing of a line drawings or a three-dimensional pointing instruction, to give an advice and a comment by use of pointing of the three-dimensional pointing mark 30, a moving image can be converted into a still image once and provided with the writing or pointing instruction as it is so that a resultant composite image of this still image may be distributed to terminals of a plurality of students to be instructed. Alternatively, conversely, in a case where a medical practitioner is helped with a surgical operation by an instructor at a remote location as receiving a writing or a pointing instruction on his monitor, a moving image distributed to the side of the instructor is converted into a still image once and provided with a writing or a pointing instruction so that a resultant composite image thereof may be distributed to the monitor of that medical practitioner.

As permitted, such a wiring or a pointing instruction can be given also to a moving image, in which case a moving image is once converted into a still image and then effectively returned to the moving image after dividing an LCD screen of the three-dimensional digital entity magnifying glass 1 so that the still image may be separately displayed into a visual field image. It should be noted that if a medical practitioner etc. serves as an instructor, such a pointing instruction or writing is typically given by a third party live-broadcasting a surgical operation by the medical practitioner or an instructor in charge in a service company of an educational system having the server 8 therein. Although a method for converting a moving image once into a still image and then returning it back to the moving image after carrying out a pointing instruction etc. as described above is known and so not detailed; in short, according to this method, an instantaneous data image from a CCD camera etc. is once accumulated in an image memory and then read and, simultaneously, an image of a pointing instruction etc. input from an input unit (which may be a moving one as well as a still one, but in some cases where a pointing instruction is moved during explanation and training, preferably the point image etc. is a moving one) is fetched so that these images may be composed using a known method such as layer processing or composition in a memory. It is thus possible to share information of a medical practitioner's three-dimensional image for a three-dimensional digital entity magnifying glass accumulated in the server 8 and information of a surgical stent image for composing and displaying a three-dimensionally accurate equal-scaled three-dimensional transparent image into a surgical field image among viewers 7a-1 through 7a-n respectively equipped with a plurality of synchronized three-dimensional digital entity magnifying glasses by utilizing a communication line such as the internet, thereby performing discussion on a three-dimensional moving image or a still image through bidirectional communication. In such communication by use of all of these images, from a viewpoint of patient's privacy protection, all of communication digital signal data is indicated on the three-dimensional digital entity magnifying glass 1 through an audio/visual decoder 4; therefore, in the case of hacking by use of an ordinary personal computer terminal having a hardware decoding unit, a risk of information leakage is low.

With this, it is possible to transmit to the educational program distribution company server 8 from the terminal personal computer 6 connected to the internet image information obtained from this digital entity magnifying glass 1, image information such as values and graphs of an illuminance, a temperature, a humidity, a pressure, and a speed that represent an environment of a situation of a vital sign of a patient in the case of a surgical operation and a situation of each technical operation in the case of the other precision techniques, voice information obtained from an audio microphone mounted on a medical practitioner, and visual instruction information such as the three-dimensional instruction mark 30.

The information received by the educational program distribution company server 8 is either directly distributed to the terminal personal computer 6 via the internet 9 or distributed in condition where image processing or interpretation in accordance with each language is performed thereon by the educational program distribution company server 8. Similarly, it is possible to transmit to the educational program distribution company server 8 from the terminal personal computer 6 connected to the internet voice information obtained from an audio microphone 1*b* of the terminal personal computer 6 and visual instruction information such as the three-dimensional instruction mark 30.

The information received by the educational program distribution company server 8 is either directly distributed to the terminal personal computers 6*a*-1 through 6*a*-*n* via the internet 9 or distributed in condition where image processing or interpretation in accordance with each language is performed thereon by the educational program distribution company server 8.

Figure 3:
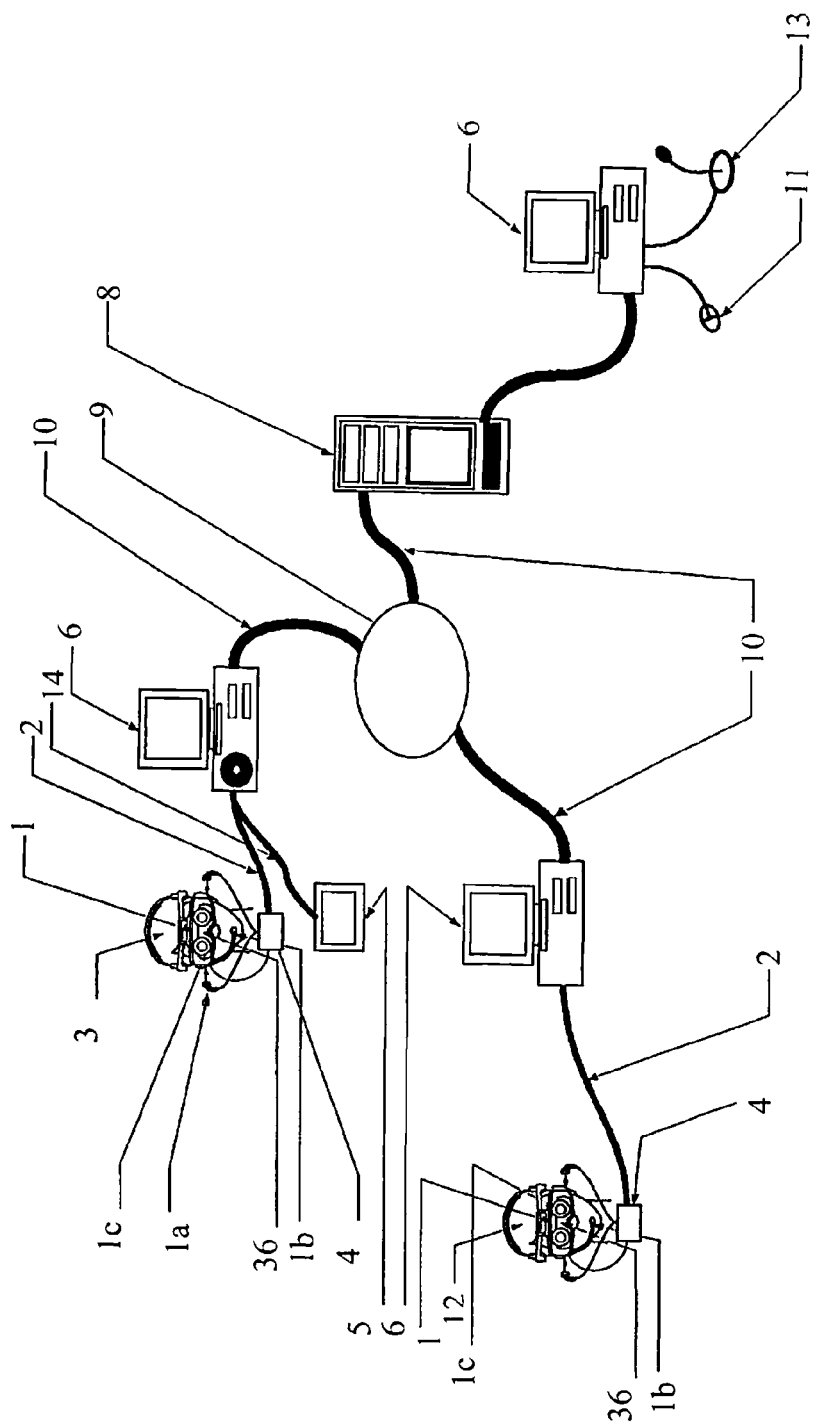
FIG. 3 is a conceptual illustration of performing communication by utilizing the internet with the digital entity magnifying glass of FIG. 1.

Next, a method for distributing information in the above-described distribution system exemplified in FIG. 1 is described along the figures in divided cases of the medical practitioner 3 (instructor) training the auditing student 12 (customer) as shown in FIG. 3 and specialized instructors (groups of lecturers) training the medical practitioner (customer) as shown in FIG. 4.

In this case where a medical practitioner (instructor) 3 performs a helping and training/educational program for a surgical operation and other precision techniques performed under direct observation on a student (customer) as shown in FIG. 3, data of the vital monitor 5 or the precision technique performing environment measurement instrument 5 and information from the audio/visual decoder 4 are composed with each other by the terminal personal computer 6 and superimposed through the audio/visual decoder 4 on a magnified image of a surgical field which is obtained from the three-dimensional CCD camera 1*c* of the three-dimensional digital entity magnifying glass 1 of FIG. 1 mounted on the medical practitioner 3 and which is projected on the eyeglass type LCD monitor 1*d* mounted on the head of the instructing medical practitioner (lecturer).

Image information which is projected to the LCD monitor 1*d* and oral instruction information for the microphone 1*b* are distributed by a specific contractant student (customer) to the terminal personal computers 7*a*-1 through 7*a*-N directly or to the technique-assisting and assisting-and training/educational distribution system distribution company server 8 from the terminal personal computer 6 by utilizing the internet 9. If the medical practitioner (instructor) and the student (customer) speak different languages, in distribution of an educational program, this information is consecutively or simultaneously interpreted into the language spoken by the student (customer) 3 and transmitted to the student (customer) by the technique-assisting and assisting-and training/educational distribution system distribution company server 8. Accordingly, a lot of specific contractant students (customers) can get a virtual experience with such realistic sensations that he feels as if he were in a field of an operating situation about a surgical operation and other highly precision oriented techniques distributed to the terminal personal computers 7*a*-1 through 7*a*-N.

Since the communication configuration can be utilized in a bidirectional manner, questions etc. of a student (customer) are verbally input with the microphone 1*b* of the terminal personal computers 7*a*-1 through 7*a*-N so that they may be transmitted in a reverse direction to the server 8 via the internet 9 and organized to eliminate duplications and then similarly transmitted to the earphone 1*a* of the instructing medical practitioner (lecturer) from the technique-assisting and assisting-and training/educational distribution system distribution company server 8 by utilizing the internet 9.

An instructing medical practitioner (lecturer) 3*a* inputs his answer to a question of a specific student (customer) into the terminal personal computer 6*a* by using the microphone 1*b*, to transmit it via the internet 9 to the technique-assisting and assisting-and training/educational distribution system distribution company server 8. Further, if the student (customer) and the medical practitioner (instructor) speak different languages, the educational program distribution company server 8 consecutively or simultaneously interprets the language spoken by the instructor into the language spoken by the student (customer) and distributes it via the internet 9 to the terminal personal computers 7*a*-1 through 7*a*-N of the students (customers).

Conversely, if specialized instructors (groups of lecturers) at a remote location guide the medical practitioner (customer) 3*b* as shown in FIG. 4, magnified surgical field image information A obtained from a two-dimensional or three-dimensional CCD camera 1*c* of the digital magnifying glass of FIG. 1 mounted on the medical practitioner (customer) 3, vital sign data B superimposed on a magnified surgical field image or image information B from a highly precision oriented technical operating environment measurement instrument, and a question C from the customer medical practitioner input through the microphone 1*b* are input through the audio/visual decoder 4 into the terminal personal computer 6 and then transmitted therefrom to the technique-assisting and assisting-and training/educational distribution system distribution company server 8 via the internet 9.

If a medical practitioner (instructor) 3*b* and the specialized instructors (groups of lecturers) 7 speak different languages, the educational program distribution company server 8 consecutively or simultaneously interprets the language spoken by the medical practitioner into that spoken by the specialized instructors (groups of lecturers) and transmit it to the specialized instructors (groups of lecturers) 7. In this case, it is transmitted via the internet 9 to terminal personal computers 7*b*-1 through 7*b*-N of one or, if technical contents cover multiple fields, a plurality of specialized instructors (groups of lecturers).

As observing magnified surgical field image information A of the medical practitioner (customer) 3 displayed on the terminal personal computers 7b-1 through 7b-N and vital sign data B superimposed on a magnified surgical field image or image information B from the highly precision oriented technical operating environment measurement instrument, the specialized instructors (groups of lecturers) 7 perform technical training and a question-and-answer session by inputting visual instructions by using the three-dimensional instruction mark 30a and oral instructions by using the microphone 1b by utilizing the terminal personal computers 7b-1 through 7b-N so that this input information may be transmitted in a reverse direction to the technique-assisting and training/educational distribution system distribution company server 8 via the internet 9 and further to the medical practitioner (customer) 3 via the internet If the specialized instructors (groups of lecturers) 12 and the medical practitioner (customer) 3 speak different languages, the educational program distribution company server 8 consecutively or simultaneously interprets the language spoken by the instructors into that spoken by the medical practitioner (customer) 3 and directly sends information of the three-dimensional instruction mark 30a onto the LCD monitor 36 of the three-dimensional digital entity magnifying glass of FIG. 1 mounted on the medical practitioner (customer) and information of the oral instruction to the earphone 1a. It is thus possible to perform bidirectional communication on a specific contractant medical practitioner (customer) 3, thereby providing skill educational training services.

Further, in FIG. 1, the terminal personal computers 6 and 7 are connected to the internet 9 and, therefore, of course are equipped with a function to access a homepage of the educational program distribution company server 8.

In such a manner, when an auditing student (customer) buys technique-assisting and training/educational programs by utilizing the homepage of the educational program distribution company server 8, he can search this homepage of the educational program distribution company server 8 for general advertisings such as histories of instructing medical practitioners (lecturers) of each of the programs, technical contents and technical fields, languages spoken by them, instruction time, and a tuition and also popularities and evaluations of students (customers) who have attended lectures already in real time, thereby obtaining unilateral promos of the instructing medical practitioners (lecturers) or objective criteria other than subjective evaluations of acquaintances who have participated in the same educational program already. Similarly, the students (customers) can apply for receiving lectures of the educational programs and pay tuition on the homepage of the educational program distribution company server 8.

Further, an instructing medical practitioner (lecturer) who teaches an educational program can utilize the homepage of the educational program distribution company server 8 to thereby give promos, accept an application for lecture reception, and confirm collection of the tuition for formal acceptance.

Conversely, in a case where a medical practitioner (customer) who wishes for receiving a lecture buys an individual technical/educational assistance and training/educational program by a plurality of field-specific expert instructors (groups of lecturers), he can search a web site of the internet homepage of the educational program distribution company for publicized technical contents and technical fields of the instructors (groups of lecturers), languages spoken by them and instruction time, and various operation-unit costs for individual technical education/training, thereby reversely nominate any one of the instructors in accordance not only with unilateral promos of the instructors (groups of lecturers) or evaluation criteria due to subjective evaluations of acquaintances who have already received a lecture of the educational program but also with objective criteria.

Moreover, tuitions are clearly published in the internet homepage web site of this educational program distribution company so that no one needs to directly negotiate about tuitions and, further, instructors (groups of lecturers) for various technical fields are organized by the educational program distribution company into an appropriate team so that the customer can get a high degree of training. Also, a medical practitioner (customer) can pay for educational training services at the internet homepage web site of this educational program distribution company.

Moreover, the instructors (groups of lecturers) can automatically receive lecture fees determined by the education program distribution company in accordance with the number of the participant instructors (groups of lecturers) for the skill educational training service lectures charged in units of operating contents or time relating to a surgical operation or any other highly precision oriented techniques, thereby keeping themselves free from troublesome office procedures.

Further, although the above description has been made on the assumption that the internet would be used, besides the internet the present invention can be applied also to communication means that connects a medical practitioner (or operator of precision work) and a party who receives information therefrom or receives it and transmits it bilaterally to each other by utilizing a closed network such as a intranet or any other dedicated line. Further, applicable communication method may use a communication satellite and any other means appropriately selected.

The present three-dimensional digital entity magnifying glass system which can enable the third party to experience virtual operations has extremely large amount of information and safe and also completely records a medical practitioner's operating situation from his visual line; therefore, if a third party uses the present system to present a surgical operation assistant on the network with conditions such as skills, experiences, and languages spoken in instruction as well as monetary rewards for above-described various services so that a staff (instructor), such as a registered medical doctor or technician, at a remote location may sign a contract and be dispatched; in this configuration, if an unexpected situation such as an error in medical treatment during a surgical operation occurs, identification of the error can be clarified based on evaluations of information recorded in the present three-dimensional digital entity magnifying glass and a responsible range is also clearly defined in accordance with contents of a contract determined beforehand based on a degree of involvement between contents of each operation and each technical field of the staff and an instruction fee presented by the medical practitioner based on the contents of a contract, thereby spreading a burden of risks for compensations for errors in medical treatment and defects.

Moreover, the present system is of a real time configuration and, at the same time, enables communication only by means of three-dimensional digital entity magnifying glasses having identical standards and, therefore, makes it very difficult to tamper data, has an extremely high degree of authenticity, and enables observing a medical practitioner's operating situation in virtual experience so that skills of the medical practitioner and existence of defects can be assessed objectively at a remote location.

An instruction image to be composed in a medical practitioner's visual field image and displayed or an anatomical three-dimensional image or surgical stent image to be composed in a medical practitioner's visual field image will not block manipulations by use of the hand or foot involved in an action of a operation by a medical practitioner or an instructor if the medical practitioner in the case of his leadership and the instructor in the case of his leadership will use an eye-contact switch or an audio command switch.

Figure 7:
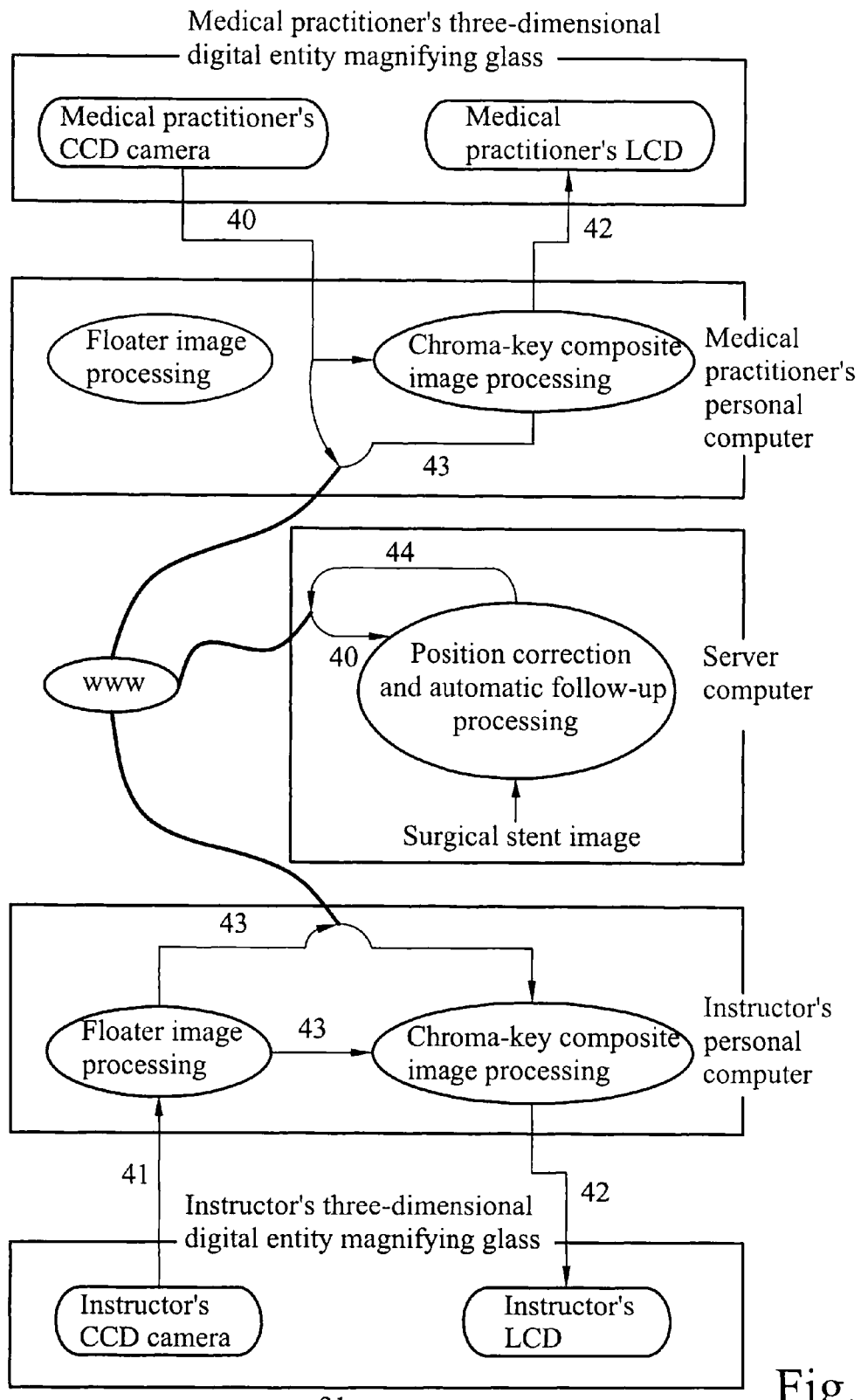
FIG. 7 is a diagram showing a flow of image information in the present system.

FIG. 7 is one example of a schematic diagram showing a situation of communication through the internet and by use of the above-described three-dimensional entity digital magnifying glass 1. As shown in this figure, visual field image information 40 from a medical practitioner's CCD camera input to a medical practitioner's personal computer is transmitted using the internet and chroma-key image-composed (42) with an instructor's CCD camera's floating image 43 transmitted from an instructor's personal computer via the internet, to display chroma-key composite image information 42 on a medical practitioner's LCD.

Similarly, the instructor can provide, in the instructor's personal computer, chroma-key composite display obtained by composing the visual field image information 40 of the medical practitioner's CCD camera transmitted through the internet displayed on the instructor's LCD and a floater-image processed image obtained from instructor's CCD camera information 41, to thereby perform training and instruction on the instructor's LCD with such a reality that as if one were performing a surgical operation by using medical apparatuses actually used. In the present system utilizing the three-dimensional digital entity magnifying glasses 1 of identical standards, by performing chroma-key composition processing on this instructor's CCD camera floating image 43 in the medical practitioner's personal computer via the internet communication line, it is possible to reflect the same image as the instructor's LCD on the medical practitioner's LCD without correcting a position of the instructor's CCD camera's floating image 43 on the medical practitioner's CCD camera's visual field image information 40.

In addition, by taking information from the medical practitioner's CCD camera into a server computer, transmitting a surgical stent floating image 44 which has undergone position correction and automatic follow-up processing to the medical practitioner's personal computer and the instructor's personal computer, and performing chroma-key composite image processing on the visual field image information 40 of the medical practitioner's CCD camera, it is possible to reflect the surgical stent image on the LCDs of the medical practitioner and the instructor. Since those manipulations are all performed on the basis of the visual field image information 40 of the medical practitioner's CCD camera, the three parties can share the same images without performing position correction. As can be seen from this schematic diagram, the medical practitioner's three-dimensional digital entity magnifying glass system and the instructor's three-dimensional digital entity magnifying glass system have totally the same functions, so that the instructor and the medical practitioner can be switched with each other easily.

It is to be noted that a configuration and a communication subject of a three-dimensional digital entity magnifying glass system of the present invention are not limited to the above-described embodiment and of course can be changed variously without deviating from the scope of the present invention.

INDUSTRIAL APPLICABILITY

A three-dimensional digital entity magnifying glass equipped with an image composition three-dimensional visual training function and a technical-assistance and training/educational distribution system of the present invention relate to a three-dimensional digital entity magnifying glass apparatus for performing technique training by utilizing a communication network such as the internet. More specifically, the present invention relates to distribution of a highly precision oriented specialized technique educational program for a surgical operation performed under direct observation of a human being or any other manual operation and a three-dimensional digital entity magnifying glass for education/training for a surgical operation performed by a specific customer or any other manually-operated highly precision oriented specialized techniques (that is, such a surgical operation or other operations is controlled through visual instructions or oral instructions by use of three-dimensional image composition based on information obtained while a visual field of a person with no technical knowledge assumed to be a robot from a remote location) and, further, enables building up a stadium system that enables chroma-key composition without using large-scale facilities even at a remote location by a medical practitioner and an instructor using three-dimensional digital entity magnifying glasses of identical standards and, at the same time, provides means for recruiting students and instructors for various kinds of educational programs and on-the-internet settlement of instruction fees for more inexpensive technique instruction and tuitions on the students.

Generally, in an educational program for live-demonstrating a surgical operation or any other manually operated specialized technique, in the case of instructing a student to perform a highly precision oriented technique such as a surgical operation by an instructor, if the technique and the surgical operation on a closed site are to be observed from identical ideal visual field as the instructing medical practitioner (lecturer), to permit the plurality of students (customers) to sequentially observe an operating situation at each step of the surgical operation, not only extremely much of time is required but also the number of persons who can observe the operation simultaneously is limited by the physical constraints of the facilities used for the operation, and such lectures have consequently been observed by very few people. In addition, if the instructing medical practitioner (lecturer) and the student (customer) speak different languages, an interpreter needs to be present during the surgical procedure, so that a fee per student (customer) for participating in such an educational program has been expensive.

Further, in the case of a surgical operation, it is difficult to transport a patient himself to a remote location for an educational program; also, in the case of other special techniques performed by hand which require large facilities or unmovable instruments, a visiting student (customer) used to arrange his schedule so as to fit in with the operating date and spend much transportation costs and time required by transportation. Moreover, when a person who wishes to receive a lecture buys an educational program, he cannot but discuss whether to buy it based only on unilateral promos of an instructing medical practitioner (lecturer) or evaluation criteria due to subjective evaluations of his acquaintances who have already received the lecture of the same educational program and, further, must separately pay a tuition through payment medium specified by each of the lecturers.

Conversely, the instructor (lecturer) who opens a course of the educational program used to provide promos by utilizing various kinds of media, accept application for reception of the lecture irrespective of whether the number of students (customers) is large or small, and confirm collection of the tuitions for formal acceptance again.

Conversely, in the case of training on a surgical operation or a practical training of highly precision oriented operation which is performed at a remote location, instructors (groups of lecturers) must go to a spot to require a lot of costs, so that various costs (transportation costs and time required by transportation) related to the training and, moreover, the remote area requiring much time to go there could not easily accommodate performing of an emergency surgical operation; especially in the case of training by a plurality of instructors (groups of lecturers), the costs used to become even higher and an emergency surgical operation used to be even more difficult to conduct. Further, if the medical practitioner (customer) and the instructors (groups of lecturers) speak different languages, it used to be necessary to take an interpreter to a field of a surgical operation.

Besides, since conducting medical treatment overseas is prohibited by legal regulations on the medical licensing, so that it is basically impossible for the instructors (groups of lecturers) to open a course of a live-operation visiting educational program in which the instructors (groups of lecturers) themselves perform a surgical operation and conduct skill training in the foreign country.

Furthermore, if a medical practitioner (customer) actually wishes to receive training of a surgical operation or any other highly precision oriented specialized techniques which are performed by hand, he cannot but select his instructors (groups of lecturers) within a limited human network and without clear criteria for calculating a tuition for each of the instructors (groups of lecturers), and he has to directly negotiate with them; therefore, he used to not only worry himself in selection of the instructors (groups of lecturers) but also have to pay the tuition through the respective payment means separately in accordance with training time and contents, thus resulting in troublesome office procedures.

Besides, when medical treatment is audited in the conventional medical fields, the present invention helps auditing consistencies between what is diagnosed and what is treated medically and is useful not only in decision of an error in medical treatment but also as criteria for calculating costs for medical treatment in a field of medical care insurances. Similarly, the present invention enables to objectively evaluate an academically surgical field (medical doctor's personal skills), so that a medical convention etc. can be held through real-time presentation on the internet, which is extremely useful in direct evaluation of competence of medical doctors, that is, establishment of criteria for selecting medical doctors accredited by the convention.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A three-dimensional digital entity magnifying glass system incorporating three-dimensional visual training functions, the system used for performing assistance and training and education under direct observation, by a medical practitioner while an instructor is watching a medical practitioner's surgical field image shared by the medical practitioner and the instructor through communication secured by use of communication means by utilizing three-dimensional digital entity magnifying glasses, which are worn by both the medical practitioner and the instructor and constituted of a pair of LCDs positioned directly in front of the two eyes and by three-dimensional digital entity magnifying glasses of identical standards indicating image information from a right-side CCD camera on the right-side LCD and image information from a left-side CCD camera on the left-side LCD of automatic focusing CCD cameras equipped with a pair of synchronized zoom lenses attached toward a visual field of the naked eye from a position that correspond to a central section between the right and left pupils of the worker wearing the magnifying glass in front of the three-dimensional digital entity magnifying glass, the system comprising:

a floater image-processing apparatus removing a background image by extracting only images of a three-dimensional pointing device which is operated by the instructor to provide visual training from a visual field image of the instructor captured by the instructor-side CCD camera on a front face of the visual field in front of the instructor-side three-dimensional digital entity magnifying glass; and an image chroma-key composite image-processing apparatus for composing and displaying a three-dimensional visual training float image, on which no background output is performed by the image-processing apparatus on the medical practitioner's visual field image captured by the CCD camera of the medical practitioner's three-dimensional digital entity magnifying glass shared by the medical practitioner and the instructor, wherein by utilizing the pair of synchronized three-dimensional digital entity magnifying glasses of identical standards worn by the medical practitioner and the instructor, the instructor provides visual training which is three-dimensional in the medical practitioner's three-dimensional visual field by utilizing images of the three-dimensional pointing device operated by the instructor which images are extracted by floating image processing from visual field images of the instructor captured by the instructor's CCD camera and chroma-key composed and displayed in the medical practitioner's visual field image captured by the medical practitioner's CCD camera projected onto an LCD monitor of the three-dimensional digital entity magnifying glass worn by the instructor.

2. The three-dimensional digital entity magnifying glass system incorporating three-dimensional visual training functions as claimed in claim 1, wherein the image chroma-key composite image-processing apparatus varies a degree of transparency of a three-dimensional visual training image of the instructor by a percentage of between 0% and 100% or changes a color tone thereof and displaying it compositely, so that the medical practitioner can easily judge training image and in order to prevent the medical practitioner's visual field and an action of an surgical operation from being blocked visually as a result of overlapping of the medical practitioner's work situation visual field image and a three-dimensional visual training image of the instructor when the floater three-dimensional visual training image with no background, output from the image chroma-key composite image-processing apparatus, of the three-dimensional pointing device operated by the instructor is chroma-key composed on medical practitioner's visual field image information in a CCD camera of the digital entity magnifying glass worn by the medical practitioner and displayed.

3. The three-dimensional digital entity magnifying glass system incorporating three-dimensional visual training functions as claimed in claim 2, further comprising an image position correction and follow-up apparatus compositely displaying three-dimensionally accurate equal-scaling three-dimensional perspective images into the medical practitioner's visual field image displayed on an LCD of a three-dimensional digital entity magnifying glass by automatically performing position correction always in respect of variations in a visual field angle of the medical practitioner with respect to a patient or to variations in postures of patients, by means of:

in an image obtained by varying a degree of transparency, by a percentage of between 0% and 100%, of image information from the medical practitioner's three-dimensional digital entity magnifying glass CCD displayed on LCDs of both the medical practitioner and the instructor;

three-dimensionally superimposing an item of three-dimensional image information obtained through image processing and conversion, by changing a three-dimensional anatomical image of an item created beforehand from information in a tomogram of a patient on whom an operation is to be performed or a surgical stent image into which the anatomical three-dimensional perspective images are three-dimensionally composed together with a dissection or bone cutting position similarly by a percentage of between 0% and 100% by varying a degree of transparency or a color tone of a site or a tissue indicative of an anatomical landmark, or by applying a visual difference to the medical practitioner's three-dimension digital entity magnifying glass CCD image information through wireframe display so as to facilitate discrimination, and onto the medical practitioner's three-dimensional digital entity magnifying glass CCD image at an equal reduction rate by utilizing a reference triangular plane obtained through three-dimensional positional measurement by use of the right and left CCDs of the three-dimensional digital entity magnifying glass and by using, as reference points, three points on non-deformable hard tissue arbitrarily determined from among the medical practitioner's three-dimensional digital entity magnifying glass CCD image information; and by enabling the anatomical three-dimensional image to automatically correct a change in position of, and follow, the reference point of the medical practitioner's three-dimensional digital entity magnifying glass CCD image information as the medical practitioner's CCD camera position changes or the patient's posture changes.

4. The three-dimensional digital entity magnifying glass system incorporating three-dimensional visual training functions as claimed in claim 3, further comprising a server storing a three-dimensional anatomical image of an arbitrary item created beforehand from information in a tomogram of a patient on whom an operation is to be performed or a three-dimensional surgical stent image in which the medical practitioner or a third party designed beforehand a position of a dissection or a bone cutting based on the anatomical three-dimensional perspective image wherein said three-dimensional image is composed into the medical practitioner's three-dimensional digital entity magnifying glass CCD'image information the remote location and accurately superimposed one on the other to provide the respective composite display images showing an apparently entity-see-through situation, positions of which images are automatically corrected by the image position correction and follow-up apparatus in real time as the medical practitioner's CCD camera position changes and the patient's posture changes, to distribute the images compositely displayed to a three-dimensionally correct position always to the medical practitioner and the instructor by utilizing communication means.

5. The three-dimensional digital entity magnifying glass system incorporating three-dimensional visual training functions as claimed in claim 3, further comprising a server accumulating the medical practitioner's three-dimensional digital entity magnifying glass'medical practitioner three-dimensional image information and surgical stent image information for compositely displaying three-dimensionally accurate equal-scaling three-dimensional perspective images into the medical practitioner's visual field image so that each of persons wearing a plurality of synchronized three-dimensional digital magnifying glasses and sharing the image information accumulated in the server can arbitrarily switch the surgical stent image information on the medical practitioner's three-dimensional digital entity magnifying glas's three-dimensional image information between a display mode and a non-display mode and, further, can transmit to the server a three-dimensional visual training image obtained by utilizing the three-dimensional digital entity magnifying glas's CCD cameras worn by them and compositely display it to the medical practitioner's three-dimensional image accumulated in the server, thereby making possible discussions through bidirectional communication on a three-dimensional moving image or a still image, by utilizing a communication line.

6. The three-dimensional digital entity magnifying glass system incorporating three-dimensional visual training functions as claimed in claim 1, further comprising a plurality of synchronized three-dimensional digital entity magnifying glasses worn by the medical practitioner and a plurality of instructors or the instructor and a plurality of medical practitioners, enabling the plurality of instructors to simultaneously guide one medical practitioner three-dimensionally by using the visual training image, or one instructor to provide visual instruction and guidance to the plurality of medical practitioners three-dimensionally.

7. The three-dimensional digital entity magnifying glass system incorporating three-dimensional visual training functions as claimed in claim 1, further comprising encryption/decryption means, wherein when distributing and publishing a training situation by use of the three-dimensional visual training image to a plurality of students other than the medical practitioner and the instructor or to a third party institution by using live-broadcasting or video-recorded broadcasting via communication means, by encrypting output signals of two right and left channels output from one three-dimensional digital entity magnifying glas's CCD camera in hardware of the three-dimensional digital entity magnifying glass and by encoding it in hardware of the other three-dimensional digital entity magnifying glass, normal image display is disabled unless a terminal having a prescribed three-dimensional digital entity magnifying glass hardware configuration is used, to provide security, thereby making possible protection of the patient's privacy.

8. The three-dimensional digital entity magnifying glass system incorporating three-dimensional visual training functions as claimed in claim 1, wherein by presenting conditions during the course of training as well as offering monetary rewards to an operation assistant on the network by using the three-dimensional digital entity magnifying glass system capable of virtually experiencing of the medical practitioner's operating situation, to sign a contract with a registered or technician to get the instructor dispatched thereto, so that if an unexpected situation during a surgical operation occurs, the unexpected situation can be clarified based on a record of information of the three-dimensional digital entity magnifying glass system and a responsible range is also clearly defined in accordance with contents of a contract determined beforehand based on a degree of involvement between contents of each operation and each technical field of the instructor and an instruction fee presented by the medical practitioner based on the contents of a contract, thereby spreading a burden of risks for compensations for the unexpected situation and defects.

9. The three-dimensional digital entity magnifying glass system incorporating three-dimensional visual training functions as claimed in claim 1, wherein it is made possible to objectively asses skills of the medical practitioner at a remote location by using the three-dimensional digital entity magnifying glass system that enables virtually experiencing an operating situation of a medical practitioner and has authenticity because the system is of a real time type and also capable of communication only by simultaneously using three-dimensional digital entity magnifying glasses of identical standards.

10. The three-dimensional digital entity magnifying glass system incorporating three-dimensional visual training functions as claimed in claim 5, further comprising a switching mechanism, wherein it is made possible to switch an instructing image compositely displayed in the medical practitioner's visual field an anatomical three-dimensional image compositely displayed in the medical practitioner's visual field image, or a surgical stent image between the display mode and the non-display mode through switching that does not block operations of using the hand or foot involved in an action of operating by the medical practitioner in the case of his leadership or through wills of the instructor in the case of his leadership.

11. A method performed in a system incorporating three-dimensional digital entity magnifying glasses which are worn by both a medical practitioner and an instructor and constituted of a pair of LCDs installed directly in front of the two eyes and used for performing assistance, and training and education under direct observation, by a medical practitioner while an instructor is watching a medical practitioner's surgical field image shared by the medical practitioner and the instructor through communication secured by use of communication means by utilizing three-dimensional digital entity magnifying glasses of identical standards indicating image information from a right-side CCD camera on the right-side LCD and image information from a left-side CCD camera on the left-side LCD of an automatic focusing CCD cameras equipped with a pair of synchronized zoom lenses which are attached toward a visual field of the naked eye from a position that nearly corresponds to a central section between the right and left pupils of the worker wearing the magnifying glass in front of the three-dimensional digital entity magnifying glass, the method comprising:

a step of floater image processing, by removing a background image by extracting only images of a three-dimensional pointing device which is operated by the instructor to provide visual instructions from a visual field image of the instructor captured by the instructor-side CCD camera on a front face of the visual field in front of the instructor-side three-dimensional digital entity magnifying glass; and a step of image chroma-key composite image processing, by composing a three-dimensional visual training float image with background output by the image-processing apparatus on the medical practitioner's visual field image captured by the CCD camera of the medical practitioner's three-dimensional digital entity magnifying glass shared by the medical practitioner and the instructor and displaying it, wherein by utilizing the pair of synchronized three-dimensional digital entity magnifying glasses of identical standards worn by the medical practitioner and the instructor, the instructor provides visual instructions which is three-dimensional in the medical practitioner's three-dimensional visual field by utilizing images of the three-dimensional pointing device operated by the instructor which images are extracted by floating image processing from visual field images of the instructor captured by the instructor's CCD camera and chroma-key composed and displayed in the medical practitioner's visual field image captured by the medical practitioner's CCD camera projected onto an LCD monitor of the three-dimensional digital entity magnifying glass worn by the instructor.

12. A three-dimensional digital entity magnifying glass system, comprising:

at least a first three-dimensional digital entity magnifying glass worn by a medical practitioner and a second three-dimensional digital entity magnifying glass worn by an instructor, wherein each three-dimensional digital entity magnifying glass comprises a right-side LCD, a left-side LCD, a right-side CCD camera on the right-side LCD, and a left-side CCD camera on the left-side LCD, and wherein a first visual field image captured by the right-side CCD camera and the left-side CCD camera of the first three-dimensional digital entity magnifying glass is displayed on the right-side LCD and left-side LCD of both the first and second three-dimensional digital entity magnifying glass;

a three-dimensional pointing device, operated by the instructor;

a floater image-processing apparatus removing a background image by extracting only images of the three-dimensional pointing device from a second visual field image captured by the right-side CCD camera and the left-side CCD camera of the second three-dimensional digital entity magnifying glass; and an image chroma-key composite image-processing apparatus receiving extracted images of the three-dimensional pointing device and composing and displaying a three-dimensional visual training float image on the first visual field image displayed on the right-side LCD and left-side LCD of both the first and second three-dimensional digital entity magnifying glass.

13. The three-dimensional digital entity magnifying glass system as claimed in claim 12, wherein each of the right-side CCD camera and the left-side CCD camera is an automatic focusing CCD camera equipped with a pair of synchronized zoom lenses.

14. The three-dimensional digital entity magnifying glass system as claimed in claim 12, wherein the image chroma-key composite image-processing apparatus varies a degree of transparency of the three-dimensional visual training float image of the instructor by a percentage of between 0% and 100% or changes a color tone of the three-dimensional visual training float image.

15. The three-dimensional digital entity magnifying glass system as claimed in claim 14, further comprising:

an image position correction and follow-up apparatus compositely displaying three-dimensionally accurate equal-scaling three-dimensional perspective images into the first visual field image.

16. The three-dimensional digital entity magnifying glass system as claimed in claim 15, wherein a three-dimensional anatomical image of an arbitrary item is superimposed into the first visual field image, wherein positions of the images are automatically corrected by the image position correction and follow-up apparatus in real time.

* * * * *